(12) United States Patent
Farhang

(10) Patent No.: US 12,702,288 B2
(45) Date of Patent: Aug. 11, 2026

(54) LARYNGOSCOPES HAVING SEPARABLE BLADES

(71) Applicant: The University of Vermont and State Agricultural College, Burlington, VT (US)

(72) Inventor: Borzoo Farhang, South Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 35 days.

(21) Appl. No.: 18/729,070

(22) PCT Filed: Jan. 30, 2023

(86) PCT No.: PCT/US2023/011869
§ 371 (c)(1),
(2) Date: Jul. 15, 2024

(87) PCT Pub. No.: WO2023/150081
PCT Pub. Date: Aug. 10, 2023

(65) Prior Publication Data

US 2025/0160635 A1 May 22, 2025

Related U.S. Application Data

(60) Provisional application No. 63/306,551, filed on Feb. 4, 2022.

(51) Int. Cl.
*A61B 1/32* (2006.01)
*A61B 1/267* (2006.01)

(52) U.S. Cl.
CPC ................ *A61B 1/32* (2013.01); *A61B 1/267* (2013.01)

(58) Field of Classification Search
CPC ....... A61B 1/32; A61B 1/267; A61B 1/00105; A61B 1/018
(Continued)

(56) References Cited

U.S. PATENT DOCUMENTS

| | | | | |
|---|---|---|---|---|
| 4,337,761 | A | 7/1982 | Upsher | |
| 4,947,829 | A * | 8/1990 | Bullard | A61B 1/267 600/101 |

(Continued)

OTHER PUBLICATIONS

International Search Report and Written Opinion dated Apr. 5, 2023, issued in connection with PCT/US2023/011869 filed on Jan. 30, 2023.

*Primary Examiner* — Jessica Weiss
(74) *Attorney, Agent, or Firm* — Downs Rachlin Martin PLLC

(57) ABSTRACT

A laryngoscope having a separable blade that includes parts that are separable from the laryngoscope so that a user can remove the laryngoscope from a patient while a medical device extending through the separable blade remains in place within the patient. In some embodiments, the separable blade includes a protective passageway that receives a medical device therethrough and protects patient tissue surrounding the laryngoscope when the laryngoscope has been inserted into a patient, and the parts of the separable blade separate from one another to open the protective passageway along its longitudinal axis. A laryngoscope of the present disclosure may include one or more features, such as a removable handle, a lighting system, and a camera system, among others. A method of using a laryngoscope having a separable blade is also disclosed.

26 Claims, 4 Drawing Sheets

(58) Field of Classification Search
USPC .................................................. 600/185–199
See application file for complete search history.

(56) References Cited

U.S. PATENT DOCUMENTS

| | | | | | |
|---|---|---|---|---|---|
| 5,261,392 | A * | 11/1993 | Wu | A61B 1/267 600/187 |
| 5,645,519 | A * | 7/1997 | Lee | A61B 1/2676 600/185 |
| 5,893,830 | A * | 4/1999 | Zeitels | A61B 1/267 600/185 |
| 7,214,184 | B2 | 5/2007 | McMorrow | |
| 8,414,481 | B2 | 4/2013 | Hakanen | |
| 9,066,700 | B2 | 6/2015 | McGrath | |
| 2011/0319718 | A1* | 12/2011 | Hakanen | A61B 1/267 600/193 |
| 2014/0323811 | A1* | 10/2014 | DeSantis | A61B 17/02 600/245 |
| 2020/0397274 | A1* | 12/2020 | Velez Rivera | A61B 1/267 |

* cited by examiner

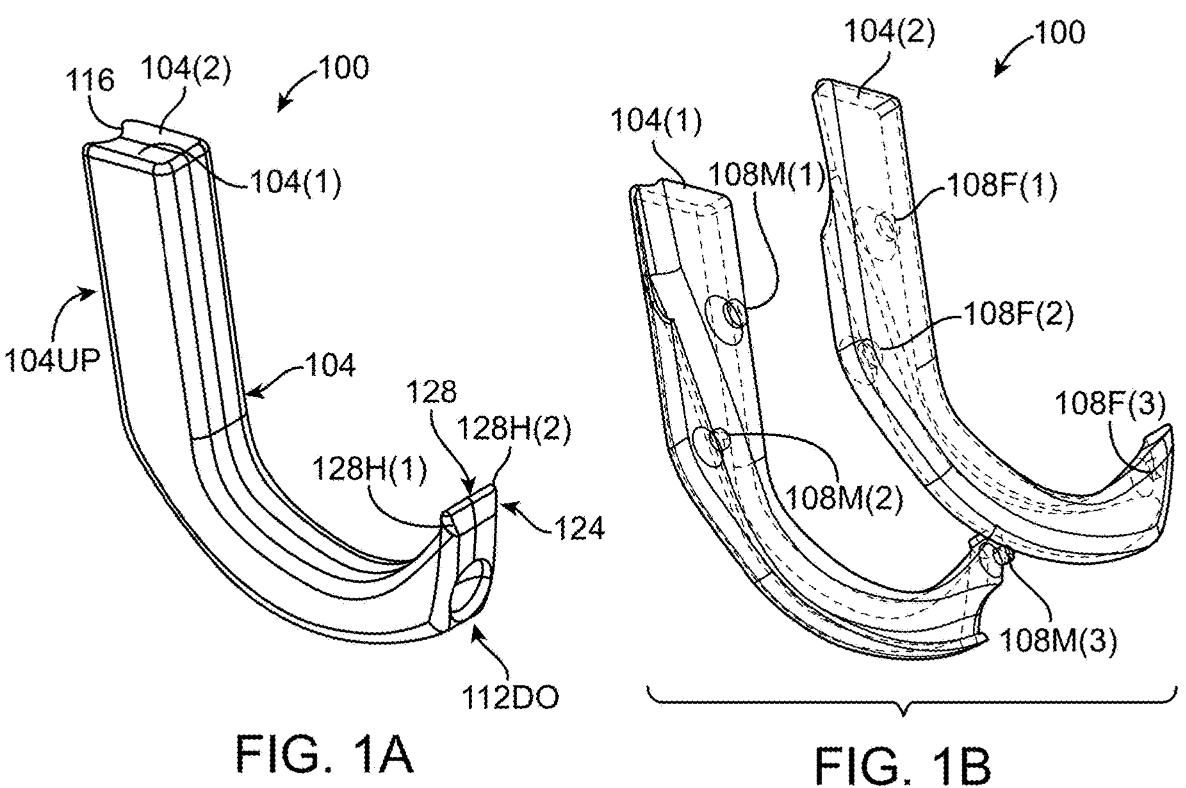
FIG. 1A
FIG. 1B
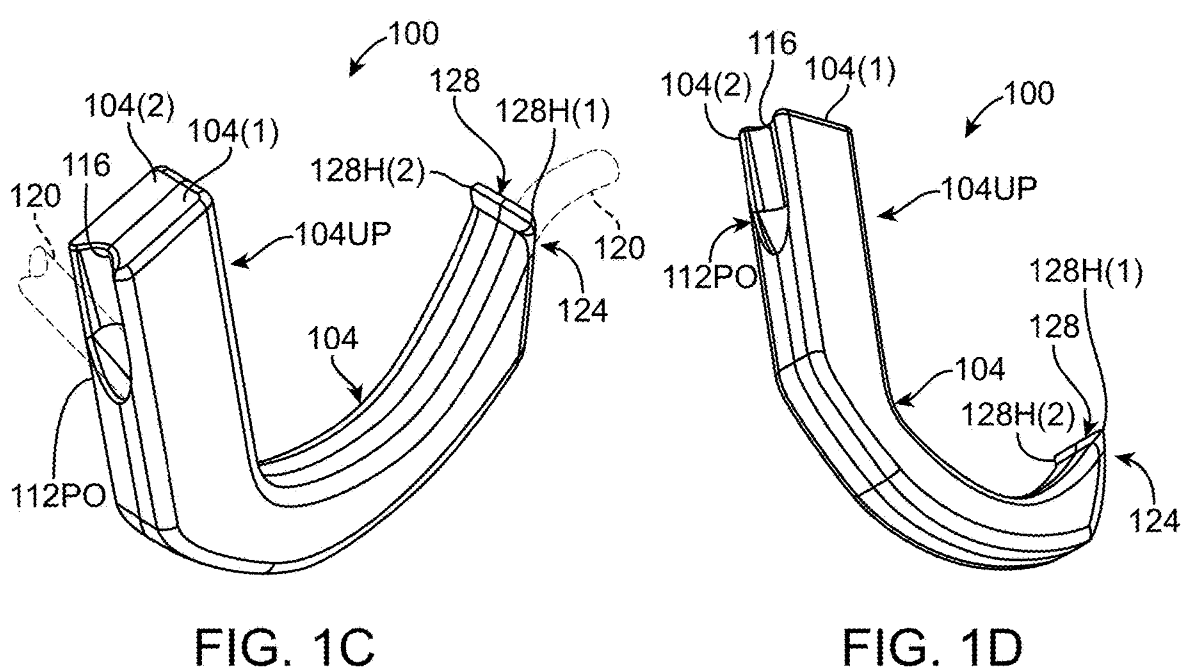
FIG. 1C
FIG. 1D

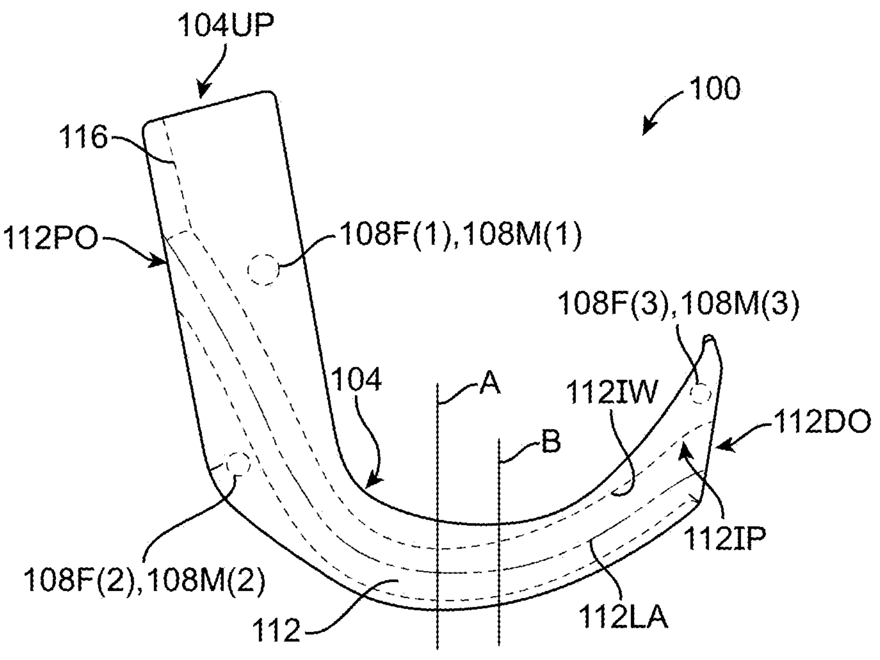
FIG. 1E
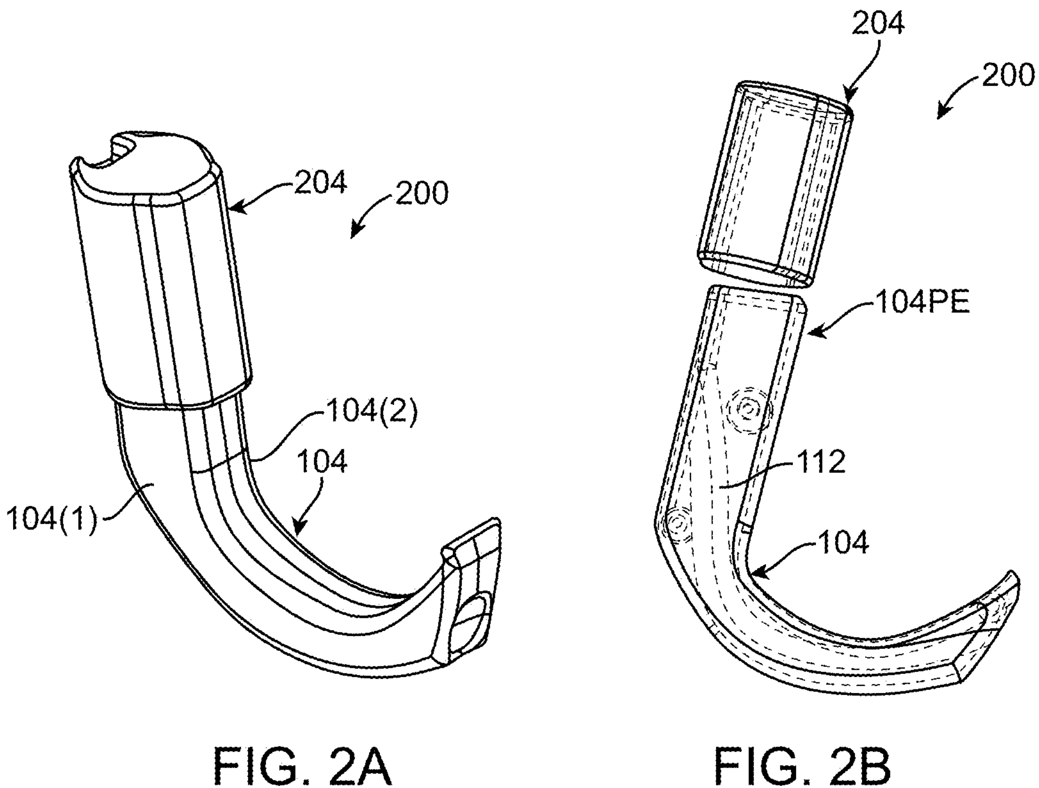
FIG. 2A
FIG. 2B

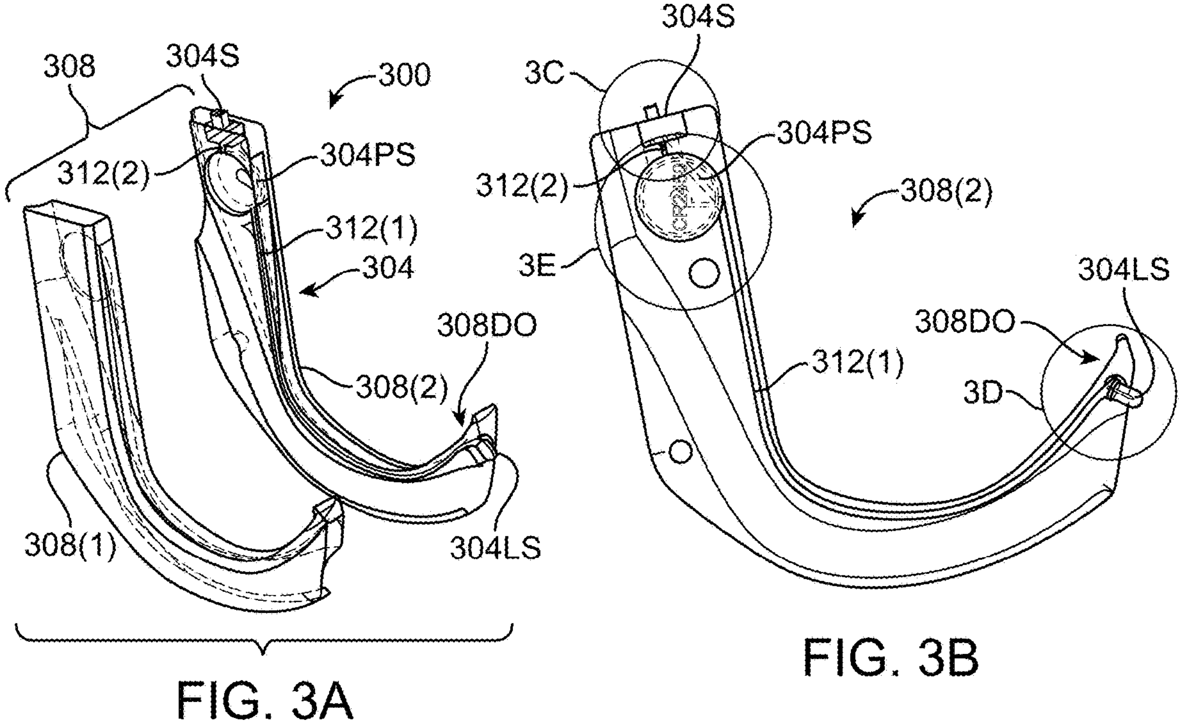
FIG. 3A
FIG. 3B
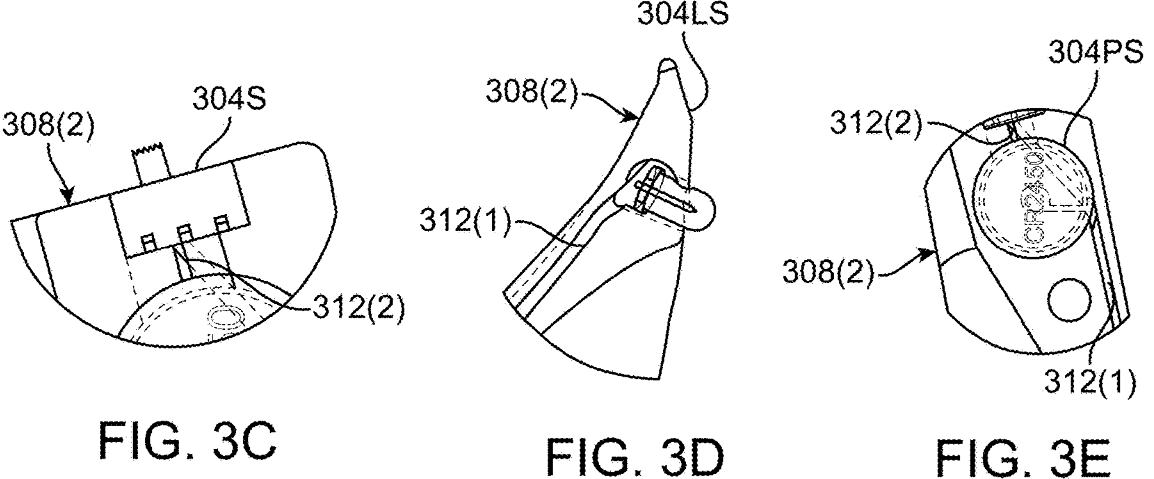
FIG. 3C
FIG. 3D
FIG. 3E

LARYNGOSCOPES HAVING SEPARABLE BLADES

RELATED APPLICATION DATA

This application claims the benefit of priority of U.S. Provisional Patent Application Ser. No. 63/306,551, filed Feb. 4, 2022, and titled "LARYNGOSCOPES HAVING SEPARABLE BLADES", which is incorporated herein by reference in its entirety.

FIELD OF THE INVENTION

The present disclosure generally relates to the field of laryngoscopy. In particular, the present disclosure is directed to laryngoscopes having separable blades.

BACKGROUND

Laryngoscopes are used in a variety of medical procedures, such as direct laryngoscopy, indirect laryngoscopy, and intubation, among others. Well-known laryngoscopes include the MacIntosh ("Mac") laryngoscope and the Miller laryngoscope invented, respectively, by Robert MacIntosh and Robert Miller. Each of the Mac and Miller laryngoscopes includes a single blade having a generally C-shaped transverse cross-sectional shape formed by an upper flange and a lower flange each connected to a lateral web. This configuration defines a longitudinal channel that is fully open to one side of the blade along the length of the blade and partially open on the bottom of the blade due to the fact that the lower flange is shorter than the upper flange. A primary difference between the Mac and Miller laryngoscopes is that the Mac version has a pronounced curvature along a significant portion of its length, whereas the Miller version is substantially straight along most of its length.

During intubation of a patient with an endotracheal tube using either a Mac or Miller laryngoscope and with the laryngoscope fully engaged with the patient, a user inserts the endotracheal tube into the patient on the open side of the C-shaped channel, which generally functions as a guide to guide the leading end of the endotracheal tube through the mouth, lower portion of the oropharynx, hypopharynx, and epiglottal region of the larynx and then through the glottis. However, since the C-shaped channel is fully open on one side and partially open on its bottom, the leading end of the endotracheal tube is directly exposed to soft tissue within the patient along the entire portion of the C-shaped channel that is inside the patient. This exposure sometimes leads to the user inadvertently damaging the soft tissue, especially when the curvature of the endotracheal tube is significantly mismatched to the curvature of the laryngoscope and/or when there are patient-specific anomalies within the oropharynx, hypopharynx, and/or epiglottal region of the larynx, such as anomalies caused by malformation, morbid obesity, prior trauma, etc. In some cases, the damage to the soft tissue can be so severe that intubation needs to be aborted and a tracheotomy needs to be performed. Soft-tissue damage during intubation using conventional laryngoscopes is known to result in morbidity and mortality.

SUMMARY

In one implementation, the present disclosure is directed to a laryngoscope, which includes a separable blade that includes: a distal end that is located proximate to a glottis of a patient during a laryngoscopy procedure; a proximal end spaced from the distal end; a protective passageway having a proximal opening at the proximal end and a distal opening at the distal end, wherein the protective passageway extends within the separable blade from the proximal opening to the distal opening along a longitudinal axis, wherein the protective passageway is configured to receive an elongate medical device therein during the laryngoscopy procedure; and two or more parts releasably secured to one another so that a user can separate the two or more parts from one another while the separable blade remains in the patient and can remove the parts from the patient while the elongated medical device, inserted into the patient via the protective passageway, remains in the patient.

In another implementation, the present disclosure is directed to a method of performing a laryngoscopy procedure on a patient having a mouth. The method includes inserting a laryngoscope having a separable blade into the patient through the patient's mouth; inserting an elongate medical device into the patient through the separable blade; and while a portion of the elongate medical device is present within the separable blade, removing the separable blade from the patient by separating parts of the separable blade from one another and withdrawing the parts from the patient through the mouth so as to leave the elongate medical device in the patient.

BRIEF DESCRIPTION OF THE DRAWINGS

For the purpose of illustration, the accompanying drawings show aspects of one or more embodiments of the invention(s). However, it should be understood that the invention(s) of this disclosure is/are not limited to the precise arrangements and instrumentalities shown in the drawings, wherein:

FIG. 1A is an isometric view of an example laryngoscope having a separable blade;

FIG. 1B is an isometric view of the laryngoscope of FIG. 1A showing parts of the separable blade separated from one another;

FIG. 1C is an isometric view of the laryngoscope of FIGS. 1A and 1B from another vantage point;

FIG. 1D is an isometric view of the laryngoscope of FIGS. 1A through 1C from yet another vantage point;

FIG. 1E is an elevational side view of the laryngoscope of FIGS. 1A through 1D showing some internal features of the laryngoscope in phantom;

FIG. 2A is an isometric view of another example laryngoscope having a separable blade, wherein the laryngoscope includes a removable handle, which is shown engaged with the separable blade of the laryngoscope;

FIG. 2B is an isometric view of the laryngoscope of FIG. 2A, showing the removable handle disengaged from the separable blade;

FIG. 3A is an isometric view of yet another laryngoscope having a separable blade, showing parts of the separable blade separated from one another;

FIG. 3B is an elevational view of one of the parts of the separable blade, showing features of that part;

FIG. 3C is an enlarged partial view of the part of FIG. 3B at detail location 3C of FIG. 3B, showing the light switch in more detail;

FIG. 3D is an enlarged partial view of the part of FIG. 3B at detail location 3D of FIG. 3B, showing the illuminator in more detail;

FIG. 3E is an enlarged partial view of the part of FIG. 3B at detail location 3E of FIG. 3B, showing the battery compartment in more detail.

DETAILED DESCRIPTION

General Description

Figure 4:
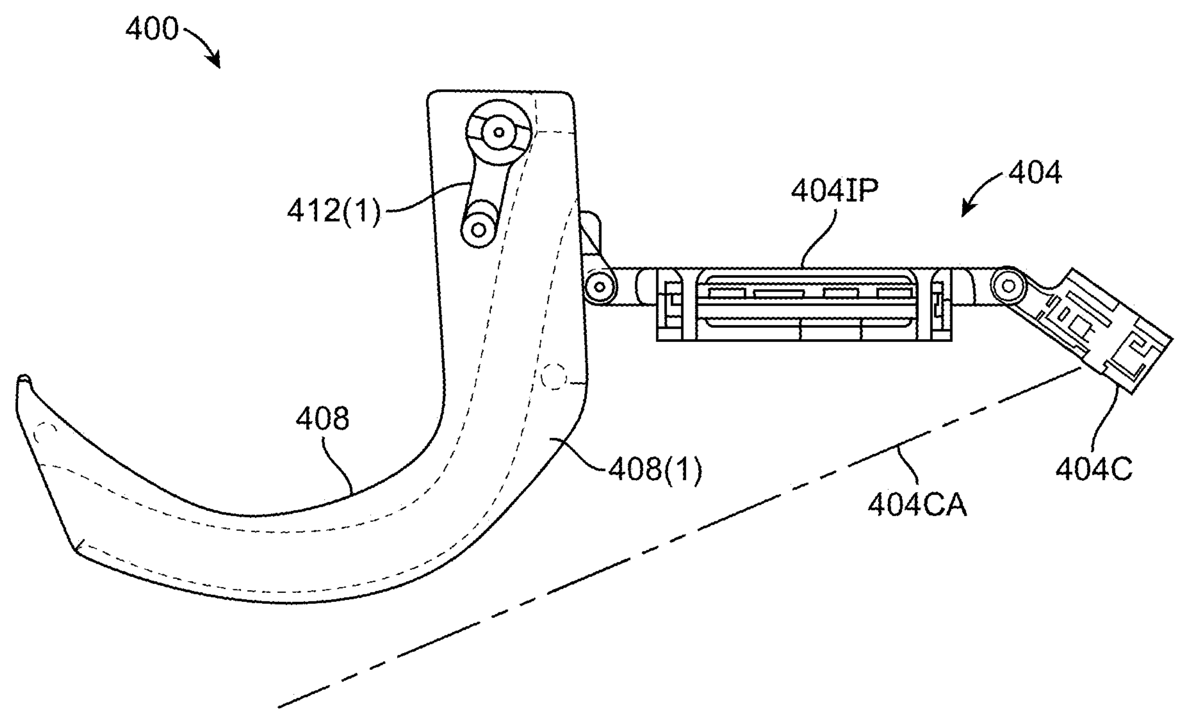
FIG. 4 is a side view of a further laryngoscope having a separable blade, wherein the laryngoscope is configured for attachment to a robotic manipulator and includes a camera mounted to the separable blade.

In some aspects, the present disclosure is directed to laryngoscopes that each include a separable blade comprising multiple parts (typically two) that are readily separable from one another by a user while the laryngoscope is in-situ within a patient, for example, after the user has already inserted and set an endotracheal tube within a patient's airway using the laryngoscope. Generally, a laryngoscope made in accordance with the present disclosure includes a separable blade and a protective passageway extending at least partway through the separable blade, with the protective passageway being sized and configured to receive therethrough any one or more of various elongate medical devices, such as an endotracheal tube, a medical scope, and a camera, among others. The multiple parts of the separable blade are releasably secured to one another so that they are separable from one another so that the entirety of the separable blade can be completely removed from a patient despite the elongate medical device remaining in place and without disturbing the elongate medical device as it remains inside the patient while the separable blade is being removed. As those skilled in the art will readily appreciate, especially after reading this entire disclosure, a separable blade of a laryngoscope of the present disclosure can be removed from a patient while an elongate medical device is still present within the protective passageway because the separating of the multiple parts (e.g., two halves), typically in directions away from one another, allows each of the multiple parts (e.g., each of the two halves) to be removed from the patient individually without disturbing the still-inserted medical device.

For simplicity, the following terms are used herein for describing embodiments of laryngoscopes of the present disclosure. The "distal end" of a laryngoscope refers to the end of the separable blade that a user first inserts into a patient during a medical procedure. In contrast, the "proximal end" of a laryngoscope is the end of the laryngoscope that remains outside of the patient during the procedure and is the end that either the user grasps while manipulating the laryngoscope during the laryngoscopy or that is engaged by another component, such as a handle or handle/battery holder, or a robotic manipulator, among other things. The term "upward curvature" and like terms, when used to describe the curvature of a separable blade and a protective passageway of this disclosure, generally refer to the nature of the curvature illustrated in FIG. 1E to the right of line A for the protective passageway 112 and to the right of line B for the separable blade when the plane of the page containing FIG. 1E is orientated vertically. The orientations "vertical" and "horizontal", when referring to a laryngoscope of the present disclosure, refer to orientations relative FIG. 1E when the plane of the page containing FIG. 1E is orientated vertically. The terms "top", "upper", "bottom", "lower", and like terms also relate to the orientation of the laryngoscope 100 shown in FIG. 1E when the plane of the page containing FIG. 1E is orientated vertically. The term "lateral" and like terms relate to direction into and out of the page containing FIG. 1E.

A separable blade of a laryngoscope of the present disclosure may be separable in any of a variety of ways to provide the requisite functionality noted above that provides the ability for a user to remove the laryngoscope while a medical device remains extending through the protective passageway. For example, a separable blade may be composed of two lateral parts, e.g., lateral halves, that are separable from one another in a generally horizontal direction. It is noted that the parts need not necessarily be true halves; rather one part may be larger than the other(s). Generally, all that is required is that once the parts are separated from one another, a user can withdraw them from the patient without removing the elongate medical device (e.g., endotracheal tube, among others, such as the others mentioned above). As another example, the separable blade may be composed of upper and lower parts that are separable from one another in a generally vertical direction. It is noted that only the portion of the laryngoscope that includes the protective passageway need be separable. For example, a proximal (e.g., upper) portion of a laryngoscope of the present disclosure need not be separable if desired for a particular design, such as, for example, a design in which a handle portion or a handle portion/battery compartment remains fully intact and attached to only one of the parts of the separable blade after separation. For example, a handle portion may be located above the protective passageway such that it does not interfere with the removal of the separated parts of the separable blades after they have been separated from one another. In other embodiments, the parts defining the separable blade and all other portions of the laryngoscope may be separable so that the laryngoscope is separable along its entire length.

The parts of the separable blade can be releasably secured to one another in any suitable manner that allows a user to separate them during the procedure utilizing the laryngoscope, preferably with little complexity and little effort. For example, the parts may be secured to one another using a friction fit, with the friction fit being effected in any one or more of a variety of ways, such as via a plurality of discretely located friction-fit components and/or a peripheral friction-fit flange arrangement extending around the entirety of the seam between parts. As another example, the parts may be secured to one another using an interference fit, which may be executed similarly to a friction fit but with interference-fit components. Friction fit and/or interference fit are particularly, though not exclusively, suitable for disposable instantiations of laryngoscopes made in accordance with the present disclosure. In still another example, one or more magnets and/or one or more ferromagnetic structures may be used in conjunction with one another to magnetically hold the parts together with one another.

In some embodiments it may be desirable to provide more robust and/or higher-longevity securing means for releasably securing the parts of a separable blade to one another. For example, such securing means may include one or more mating interference structures that require a release mechanism to move or release one or more interfering components that create the interference. Such a release mechanism may be, for example, a mechanical release mechanism, an electromechanical release mechanism, or an electromagnetic release mechanism, among others, that include one or more user-actuatable release controls, such as one or more release buttons. Such mechanisms would typically add complexity to a laryngoscope. However, in some cases, such as reusable embodiments, the additional production costs associated with the additional complexity may be justified.

It is noted that any two or more suitable ones of the foregoing releasable securing means for releasably securing the parts of a separable blade of the present disclosure may be used with one another. In any case, the amount of effort needed to separate the parts, as well as the duty cycle (e.g., single use versus multiuse) of the separability can be engineered into any securement means selected using routine skill in the art.

The protective passageway of a laryngoscope of the present disclosure is configured to prevent an elongate medical device being inserted into the patient through the separable blade during a procedure from contacting any of the patient's soft tissue that immediately surrounds the separable blade. Thus, the protection that the protective passageway affords is protection of soft tissue and provides 360° "all-around" protection, as viewed from the longitudinal axis of the protective passageway. The protective passageway may be configured in any suitable way that allows the user to insert the relevant medical device therethrough. For example, the protective passageway may have a continuously curved (e.g., circular, elliptical, oval, etc.) transverse (i.e., transverse to the longitudinal axis of the protective passageway) cross-sectional shape and have a continuous smooth wall. That said, other transverse cross-sectional shapes, such as polygonal shapes (e.g., hexagonal, octagonal, etc.), can be used, and the wall(s) need(s) not be smooth and/or continuous. Regarding the latter, an example of a non-smooth wall is one that is splined, and an example of a non-continuous wall is one that is fenestrated with one or more openings extending from the protective passageway to the exterior of the separable blade.

In some embodiments, the distal end of the separable blade includes a beak region that is configured to assist the user with manipulating a patient's epiglottis during a laryngoscopy procedure. Generally, the beak region has a tip configured to provide an epiglottal hook that allows the user to hook a portion of the beak region behind the epiglottis on its glottal side to facilitate retracting the epiglottis away from the glottis. In some embodiments, an epiglottal hook includes a cylindrical structure located transversely on the generally upwardly disposed tip of the beak region, with the lateral ends of the cylindrical structure extending slightly beyond the corresponding lateral sides of the separable blade to provide slightly outstanding horns on the two lateral sides of the separable blade. Such horns can enhance the ability of the beak to hold an epiglottis relative to the separable blade so as to inhibit the epiglottis from slipping off of the upper surface of the separable blade. It is noted that the tip of the beak region need not include any additional structure (such as the cylindrical structure) and/or does not need to include any horns that extend laterally from the lateral sides of the beak region.

In some embodiments, a laryngoscope made in accordance with the present disclosure may be configured to carefully guide an elongate medical device (e.g., an endotracheal tube, among others) through a patient's glottis when the separable blade is properly engaged with the epiglottis. The carefully considered configuration may include specially configuring the distal end of the separable blade. For example, the special configuration may include locating the top of the distal opening of the protective passageway at a suitable distance down from the tip of the beak and providing the protective passageway with an inflection point in its curvature whereat the curvature of the protective passageway changes from upwardly curved to downwardly curved. An example of this is illustrated in FIG. 1E and described below. This change in curvature can act to direct a leading end of the elongated medical device being inserted into the patient through the protective passageway along a trajectory as it exits the protective-passageway opening that passes as centrally as possible through a patient's glottic opening. This will tend to minimize the chance of the leading end of the elongate medical device contacting and potentially damaging soft tissue along that trajectory beyond the protective passageway.

As those skilled in the art can appreciate, while some elongate medical devices, such as endotracheal tubes, can be manipulated to pre-curve the elongate medical device prior to inserting into the patient, the induced pre-curvature does not typically match the curvature that is optimal for insertion into a patient via a laryngoscope. Providing the reverse in curvature toward the distal end of the separable blade can effectively force the curvature of the elongate medical device to be closer to optimal. It is noted that a single design of a laryngoscope of the present disclosure may be provided in differing sizes to accommodate, for example, patients of different sizes and/or anatomical differences within the mouth, pharynx, and/or larynx of different patients. Those skilled in the art will readily be able to design separable blades and laryngoscopes of differing sizes based on their anatomical knowledge and the general principles disclosed herein.

As can be seen in the appended figures, each of the example laryngoscope instantiations shown there has the general curved shape of a conventional Mac laryngoscope. It is noted, however, that this need not be so, as other overall curvatures can be adopted. For example, a laryngoscope made in accordance with the present disclosure may have a straighter configuration, such as in the manner of a conventional Miller laryngoscope, among others.

A laryngoscope of the present disclosure may be made of any one or more suitable materials. Example materials include, but are not limited to, various thermoplastic polymers and/or thermoset polymers (including blends thereof) (either reinforced or unreinforced) and medical grade metals, such as stainless steel, among others. In some embodiments, a laryngoscope of the present disclosure is designed and constructed to be of a single-use disposable type. For this type, the entire laryngoscope may be made of a suitable recyclable polymer. In some embodiments, a laryngoscope of this disclosure may be designed and constructed to be of a multi-use non-disposable type that must be more robust and readily sterilizable. For this type, the separable blade may be made of one or more metals and/or one or more robust polymers. In some embodiments, the laryngoscope may include a handle that is either removably engageable with the separable blade or permanently attached to the separable blade as discussed above.

As illustrated in some of the example instantiations of the appended figures, which are described in more detail below, a laryngoscope made in accordance with the present disclosure may include any one or more of a variety of features, such as, but not limited to, an onboard or otherwise integrated or partially integrated lighting system, an onboard or otherwise integrated or partially integrated camera system, an integrated handle, one or more robotic-manipulator attachment features, and any suitable combination thereof, among others.

Example Laryngoscope Instantiations

In the example laryngoscopes 100, 200, 300, and 400 shown in FIGS. 1A through 4 of the appended drawings, all of the descriptions of laryngoscopes and features thereof in the foregoing GENERAL DESCRIPTION section that fall within the scope of the present disclosure apply, as they are pertinent to a particular embodiment, to each of the example instantiations. In addition, where any of the example laryngoscopes 100, 200, 300, and 400 does not include one or more features discussed above, those skilled in the art will readily be able to determine whether each of the non-included features is suitable for that laryngoscope and, if that feature is suitable for that laryngoscope, how to modify the laryngoscope at issue. Similarly, those skilled in the art will readily be able to determine whether a feature that any of the laryngoscopes 100, 200, 300, and 400 is shown and/or described as having can be eliminated in a modified version. Further, those skilled in the art will readily appreciate that any specific feature of any of the example laryngoscopes 100, 200, 300, and 400 for which alternatives are mentioned above in the GENERAL DESCRIPTION section can be replaced by any of the mentioned alternatives or equivalent thereto.

FIGS. 1A through 1E show a first example laryngoscope 100 made in accordance with the present disclosure. In this example, the laryngoscope 100 includes a separable blade 104 having two parts 104(1) and 104(2) that are separable from one another and form the entirety of the separable blade. In this example, the two parts 104(1) and 104(2) are generally true halves, with the exception of the releasable securing means, which here, and best seen in FIG. 1B, are a set of three male friction-fit structures 108M(1) through 108M(3) and a corresponding set of three female friction-fit structures 108F(1) through 108F(3) sized and configured to slidingly receive the corresponding male friction-fit structures. In this embodiment, the upper portion 104UP of the separable blade 104 functions as a handle for the user during the process of inserting the laryngoscope 100 into a patient.

The laryngoscope 100 includes a protective passageway 112 (FIG. 1E) having a proximal opening 112PO and a distal opening 112DO, with the protective passageway extending within the separable blade 104 between these two openings when the two parts 104(1) and 104(2) are engaged with one another. The protective passageway 112 has a generally circular transverse cross-sectional shape. In this embodiment, the upper end 104UP of the separable blade 104 includes a circularly curved (in transverse cross-section) channel 116 above the proximal opening 112PO of the protective passageway to assist the user with inserting a medical device 120 (FIG. 1C) into the laryngoscope.

Referring to FIG. 1E, it is readily seen that the protective passageway 112 has a longitudinal axis 112LA that is curved, with the curvature of the longitudinal axis and the protective passageway itself being generally upward to the right of line A. The curvature of the inner wall 112IW of the protective passageway 112 includes an inflection point 112IP where the curvature changes from upward to downward. As discussed above in the GENERAL DESCRIPTION section, this inflection point 112IP and corresponding change in curvature of the protective passageway 112 can aid in causing the medical device 120 (FIG. 1C), as it exits the distal opening 112DO, to proceed on a trajectory that is less likely to cause damage to a patient's soft tissue. The precise location of the inflection point 112IP and the amount of the downward curvature past the inflection point can vary depending on any one or more factors, such as the overall shapes and/or sizes of the laryngoscope 100 and protective passageway 112 and the size, type, and flexibility characteristics of the medical device 120 (FIG. 1C), among others. FIG. 1E also shows some example dimensions, in millimeters, for some of the aspects of the example laryngoscope 100. Those skilled in the art will readily understand that the dimensions shown are merely examples and non-limiting.

Referring particularly to FIGS. 1A, 1C, and 1D, the example laryngoscope 100 includes a beak region 124 that includes an epiglottal hook 128. In this example, the epiglottal hook 128 is generally in the form of a cylinder and includes horns 128H(1) and 128H(2) projecting laterally from the separable blade 104. As discussed above in the GENERAL DESCRIPTION section, the epiglottal hook 128 and horns 128H(1) and 128H(2) can assist a user of the laryngoscope 100 with manipulating a patient's epiglottis. Those skilled in the art will readily be able to select the amount that each horn 112H(1) and 112H(2) projects beyond the separable blade 104 using ordinary skill in the art and/or routine testing.

FIGS. 2A and 2B illustrate a laryngoscope 200 that is similar to the laryngoscope 100 of FIGS. 1A through 1E but that further includes a removable handle 204 in addition to the separable blade 104. FIG. 2A shows the laryngoscope 200 with the removable handle 204 in its fully engaged position relative to the separable blade 104, whereas FIG. 2B shows the removable handle disengaged from the separable blade. In this instantiation, a user (not shown) can insert the separable blade 104 into a patient (not shown) with the removable handle 204 in its fully engaged position (FIG. 2A). Indeed, as long as the user does not need to use the blade-separation feature of the laryngoscope 200, the user will typically keep the removable handle 204 in the fully engaged position (FIG. 2A) during the entire laryngoscopy procedure from insertion, to epiglottal manipulation, through any insertion and removal of an elongate medical device 120 (FIG. 1C) through the protective passageway 112, and to extraction of the intact separable blade 104. However, if the user desires/needs to use the blade-separation feature to separate the parts 104(1) and 104(2) of the separable blade 104, then the user would first remove the removable handle 204 and thereafter separate the parts 104(1) and 104(2) of the separable blade as generally seen in FIG. 1B.

The removable handle 204 may snugly receive the proximal end 104PE (FIG. 2B) of the separable blade 104 and function to hold the parts 104(1) and 104(2) (FIG. 2A) of the separable blade 104 in firm contact and/or alignment with one another while it is fully engaged with the separable blade. In alternative embodiments, the removable handle 204 alone may function as the securing means that holds the parts 104(1) and 104(2) of the separable blade 104 together. The removable handle 204 may be secured to the separable blade 104 by, for example, friction fit and/or interference fit, among other handle-securing means. Any handle-securing means provided may be the same as or similar to the releasably securing means discussed above in the GENERAL DESCRIPTION section.

FIGS. 3A through 3E illustrate laryngoscope 300 (FIG. 3A) that is similar to the laryngoscope 100 of FIGS. 1A through 1E, except that the laryngoscope 300 of FIGS. 3A through 3E incorporates an onboard lighting system 304 for providing light at the distal end 308DO of the separable blade 308 that comprises parts 308(1) and 308(2). Some uses of a laryngoscope can be enhanced when more light than the ambient light that can enter through and beneath the laryngoscope is needed. The instantiation of FIGS. 3A through 3E provide the user with a convenient means of providing that additional light. In this example, the onboard lighting system 304 includes one or more light sources (one light source 304LS shown), such as one or more light-emitting diodes (LEDs), a power source 304PS, such as one or more primary or secondary batteries, a switch 304S, such as, for example, a slide switch (shown), a toggle switch, a rocker switch, or a push-button switch, among others, to allow the user to switch the light source on and off as needed/desired, and any circuitry, such as wiring (e.g., wires 312(1) and 312(2), transformer, current/voltage conditioner, etc. needed to complete the onboard lighting system. FIGS. 3C through 3E show, respectively, more detailed views of the switch 304S, the light source 304LS, and the power source 304PS. Those skilled in the art will readily appreciate that the onboard lighting system 304 of the laryngoscope 300 of FIGS. 3A through 3E is merely illustrative and that many variations are possible, including variations having different light sources, more than one light source, different light-source location(s), offboard power sources, etc.

FIG. 4 shows a laryngoscope 400 that, for illustrative purposes only, is based on the laryngoscope 100 of FIGS. 1A through 1E but is adapted for connecting to a robotic manipulator (not shown) and includes an integrated camera system 404 for capturing images inside a patient's larynx (not shown). Such images can be used, for example, to guide the separable blade 408 of the laryngoscope 400 into the patient, among other things. In the embodiment shown, the integrated camera system 404 includes a camera 404C that is located, positioned, and aimed so that, when the separable blade 408 is properly inserted for a direct laryngoscopy, the imaging axis 404CA of the camera extends through the glottis beneath the separable blade in the spaces within the patient between the anterior portion of the pharynx and the separable blade in order to provide the camera with a direct view of the patient's glottal region. Also in this embodiment, the camera system 404 includes an onboard image processor 404IP, here positioned between the camera 404C and the separable blade 408. In other embodiments, the onboard image processor 404IP may be located elsewhere on the laryngoscope 400 or the image processing may be performed offboard of the laryngoscope 400. The onboard image processor 404IP and/or camera 404C may communicate wirelessly or wiredly with one or more offboard systems (not shown) as needed. The onboard camera system 404 may be attached to the separable blade 408 in any suitable manner. It is noted that the camera system illustrated in FIG. 4 can alternatively be adopted on handheld versions of laryngoscopes of the present disclosure.

As noted above, the laryngoscope 400 of FIG. 4 is adapted for use with a robotic manipulator (not shown) and includes an attachment structure on each of the two separable parts (e.g., like the parts 104(1) and 104(2) of the laryngoscope 100 of FIGS. 1A through 1E) forming the separable blade 408 for attaching the laryngoscope to the robotic manipulator. In FIG. 4, only the attachment structure 412(1) of one part 408(1) is seen, with another attachment structure located on the other part of the separable blade 408. The unseen attachment structure may be the same as or different from the attachment structure 412(1), and both attachment structures may be any structure suitable for attaching the laryngoscope 400 to the robotic manipulator 400.

Example Use of a Laryngoscope Having a Separable Blade

In an example method of using a laryngoscope having a separable blade of the present disclosure, such as, for example, any of the laryngoscopes 100, 200, 300, and 400 of FIGS. 1A through 4, a user (e.g., a human or a robot-assisted human) (not shown), may insert the laryngoscope into a patient using any suitable insertion technique, such as a technique similar to a recommended insertion technique for a Mac or Miller laryngoscope, among others. Once the laryngoscope is generally in its proper position with the tip of the separable blade behind the epiglottis, the user may decide to perform a direct laryngoscopy, for example, by retracting the epiglottis and attempting a direct view of the glottal region through the space between the bottom of the separable blade and the posterior portions of the pharynx and pharyngeal end of the larynx. If the laryngoscope is provided with an onboard lighting system, the direct-view laryngoscopy may be augmented by light from the onboard lighting system.

For some patients, a suitable direct-view laryngoscopy cannot be obtained, and the user may decide to switch to an indirect laryngoscopy with the assistance of an indirect viewing device, such as a medical scope or camera. The user may insert the indirect viewing device into the patient via the protective passageway of the separatable blade, with or without using a separate tube sleeve for the indirect viewing device. Depending on the availability of a light source on the indirect viewing device, if the laryngoscope has a lighting system, the indirect laryngoscopy may be assisted using light from that lighting system.

At some point, the user may decide that the patient needs to be intubated for breathing. If an endotracheal tube is already present within the protective passageway of the separable blade but not fully inserted into the patient's airway, then the user will fully insert the tube and then inflate the cuff as usual. If an endotracheal tube is not yet present within the protective passageway of the separable blade, then the user will engage the tube within the protective passageway of the separable blade, fully insert the tube into the patient's airway via the protective passageway, and inflate the cuff as usual. Once the endotracheal tube has been fully inserted and the cuff inflated, the proper position of the endotracheal tube is confirmed, and then the user can remove the laryngoscope by separating the parts of the separable blade from one another and withdrawing them from the patient. Depending on the design of the laryngoscope, before the user can separate the parts of the separable blade from one another, the user may need to perform one or more other actions, such as remove a handle and/or a battery holder engaged with separable blade and/or actuate a release mechanism, among other things.

Those skilled in the art will readily understand that the foregoing example use of a laryngoscope of the present disclosure is presented simply as a nonlimiting example, as skilled artisans will fully understand how to adopt a laryngoscope of the present disclosure to any medical procedure they may perform therewith.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A laryngoscope, comprising:

a separable blade that includes:

a distal end that is configured to be located proximate to a glottis of a patient during a laryngoscopy procedure;

a proximal end spaced from the distal end along a longitudinal axis, wherein, between the proximal and distal ends, the separable blade has a curvature along the longitudinal axis and in a plane containing the longitudinal axis;

a protective passageway having a proximal opening at the proximal end and a distal opening at the distal end, wherein the protective passageway extends within the separable blade from the proximal opening to the distal opening along the longitudinal axis, wherein the protective passageway is configured to receive an elongate medical device therein during the laryngoscopy procedure; and a pair of laterally separable parts releasably secured to one another so that a user can separate the pair of laterally separable parts from one another laterally in a direction perpendicular to the plane while the separable blade remains in the patient and, following the separating, can remove the pair of laterally separable parts from the patient while the elongated medical device, previously inserted into the patient via the protective passageway, remains in the patient.

2. The laryngoscope of claim 1, wherein the protective passageway is configured to provide 360° protection, relative to the longitudinal axis, to tissue of the patient surrounding the separable blade from the elongate medical device when the separable blade is present within the patient and the elongate medical device is inserted into the protective passageway.

3. The laryngoscope of claim 1, wherein the distal end includes a beak region that includes an epiglottal hook.

4. The laryngoscope of claim 3, wherein the separable blade has a pair of spaced- apart lateral sides, and the epiglottal hook includes a pair of horns extending laterally beyond the spaced-apart lateral sides of the separable blade.

5. The laryngoscope of claim 1, wherein:

the distal end includes a beak region having a tip;

the distal opening is spaced from the tip of the beak region; and the protective passageway includes an inflection point proximate to the distal opening and at which a curvature of the protective passageway changes from an upward curvature to a downward curvature.

6. The laryngoscope of claim 5, wherein the beak region, the inflection point, the downward curvature, and the distal opening are configured so that, when the tip is engaged with an epiglottis during the laryngoscopy procedure, the protective passageway directs the elongate medical device toward a glottic opening of the patient.

7. The laryngoscope of claim 1, wherein the pair of laterally separable parts includes a pair of blade halves that are substantially mirror images of one another.

8. The laryngoscope of claim 7, wherein the friction fit is effected by a plurality of mating friction-fit structures on each of the pair of laterally separable parts.

9. The laryngoscope of claim 1, wherein the pair of laterally separable parts are releasably secured to one another by friction fit.

10. The laryngoscope of claim 1, wherein the pair of laterally separable parts are releasably secured to one another by interference fit.

11. The laryngoscope of claim 10, wherein the interference fit is effected by a plurality of mating interference-fit structures on each of the pair of laterally separable parts.

12. The laryngoscope of claim 1, wherein the pair of laterally separable parts are releasably secured to one another using one or more magnets.

13. The laryngoscope of claim 1, further comprising a releasable securing means for releasably securing the pair of laterally separable parts to one another.

14. The laryngoscope of claim 13, wherein the releasable securing means is selected from a group consisting of a mechanical mechanism, an electronic mechanism, and an electromechanical mechanism.

15. The laryngoscope of claim 1, further comprising an onboard lighting system.

16. The laryngoscope of claim 15, wherein the onboard lighting system includes a light source located at the distal end of the separable blade.

17. The laryngoscope of claim 1, further comprising a removable handle removably engaged with the separable blade so that removal of the handle from the separable blade frees the pair of laterally separable parts so that the user can laterally separate the pair of laterally separable parts from one another.

18. The laryngoscope of claim 1, further comprising an onboard camera system designed, configured, and located for imaging a region adjacent to the separable blade.

19. The laryngoscope of claim 18, wherein the region is a glottal region of the patient.

20. A method of performing a laryngoscopy procedure on a patient having a mouth, the method comprising:

inserting a laryngoscope having a separable blade into the patient through the patient's mouth, wherein the separable blade has a length and an upward curvature along the length;

inserting an elongate medical device into the patient through the separable blade; and while a portion of the elongate medical device is present within the separable blade, removing the separable blade from the patient by laterally separating parts of the separable blade from one another in a direction perpendicular to the upward curvature and withdrawing the parts from the patient through the mouth so as to leave the elongate medical device in the patient.

21. The method of claim 20, further comprising, after inserting the laryngoscope, performing a direct laryngoscopy by gazing under the bottom of the separable blade.

22. The method of claim 20, wherein the patient further has a glottic opening and an epiglottis and the method further includes retracting the epiglottis away from the glottic opening using a beak region of the separable blade.

23. The method of claim 22, wherein the beak region is configured to provide an epiglottal hook.

24. The method of claim 23, wherein the separable blade has a pair of lateral sides spaced from one another, and the epiglottal hook includes a pair of horns extending laterally beyond respective ones of the lateral sides.

25. The method of claim 20, wherein separating parts of the separable blade includes separating the parts in a lateral direction.

26. The method of claim 25, wherein the parts include a pair of blade halves.

* * * * *